United States Patent
Nielsen et al.

(10) Patent No.: US 10,278,923 B2
(45) Date of Patent: May 7, 2019

(54) ORAL DOSING OF GLP-1 COMPOUNDS

(71) Applicant: Novo Nordisk A/S, Bagsvaerd (DK)

(72) Inventors: Flemming S. Nielsen, Roskilde (DK); Per Sauerberg, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/651,043

(22) Filed: Jul. 17, 2017

(65) Prior Publication Data

US 2017/0312225 A1 Nov. 2, 2017

Related U.S. Application Data

(63) Continuation of application No. 14/785,493, filed as application No. PCT/EP2014/058974 on May 2, 2014, now abandoned.

(30) Foreign Application Priority Data

May 2, 2013 (EP) .................... 13166205

(51) Int. Cl.
| | | |
|---|---|---|
| A61K 38/26 | (2006.01) | |
| A61K 38/00 | (2006.01) | |
| A61K 38/22 | (2006.01) | |
| A61K 38/12 | (2006.01) | |
| A61K 9/20 | (2006.01) | |
| A61K 9/00 | (2006.01) | |
| A61P 3/04 | (2006.01) | |
| A61P 3/10 | (2006.01) | |

(52) U.S. Cl.
CPC .......... *A61K 9/2013* (2013.01); *A61K 9/0053* (2013.01); *A61K 38/26* (2013.01); *A61P 3/04* (2018.01); *A61P 3/10* (2018.01); *A61K 9/2054* (2013.01)

(58) Field of Classification Search
None
See application file for complete search history.

(56) References Cited

U.S. PATENT DOCUMENTS

| | | |
|---|---|---|
| 9,278,123 B2 | 3/2016 | Sauerberg et al. |
| 2009/0088369 A1 | 4/2009 | Steiness |
| 2013/0053311 A1 | 2/2013 | Kalthoff et al. |
| 2016/0151462 A1 | 6/2016 | Sauerberg et al. |

FOREIGN PATENT DOCUMENTS

| | | |
|---|---|---|
| EP | 2565202 A1 | 3/2013 |
| WO | 0066629 A1 | 11/2000 |
| WO | 0248192 A2 | 6/2002 |
| WO | 2005014049 A2 | 2/2005 |
| WO | 2006097537 A2 | 9/2006 |
| WO | 2007024700 A2 | 3/2007 |
| WO | 2007067964 A2 | 6/2007 |
| WO | 2008033888 A2 | 3/2008 |
| WO | 2010020978 A1 | 2/2010 |
| WO | 2012140117 A1 | 10/2012 |
| WO | 2013009545 A1 | 1/2013 |

OTHER PUBLICATIONS

Beglinger et al. 2010. Am. J. Clin Nutr. 92:810-7 (Year: 2010).*
Fonseca et al. 2012. Diabetes Care. 35:1225-1231 (Year: 2012).*
Steinert et al., 2010, Am J Clin Nutr, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.

* cited by examiner

*Primary Examiner* — Shulamith H Shafer
(74) *Attorney, Agent, or Firm* — Nonna G. Akopyan

(57) ABSTRACT

The present invention relates to improved uses of GLP-1 peptides in oral therapy.

23 Claims, No Drawings

ORAL DOSING OF GLP-1 COMPOUNDS

CROSS-REFERENCE TO RELATED APPLICATIONS

This application is a Continuation of U.S. application Ser. No. 14/785,493, filed Oct. 19, 2015, which is a 35 U.S.C. § 371 National Stage application of International Application PCT/EP2014/058974, filed May 2, 2014, which claims priority to European Patent Application 13166205.8, filed May 2, 2013; all of which are hereby incorporated by reference.

TECHNICAL FIELD

The present invention relates to improved uses of GLP-1 peptides in oral therapy.

BACKGROUND

The oral route is by far the most widely used route for drug administration. Administration of peptides and proteins, such as GLP-1 peptides, is however often limited to parenteral routes rather than the preferred oral administration due to several barriers, such as enzymatic degradation in the gastrointestinal tract and intestinal mucosa, insufficient absorption from the intestinal mucosa, as well as first pass metabolism in the liver.

WO2007/024700 relates to methods for reducing body weight and treating diabetes by the use of exendin peptides.

There is thus a need for an improved method for administering or use of GLP-1 peptides by the oral route where variability in plasma concentration is acceptable.

SUMMARY

In some embodiments the present invention relates to a solid composition comprising a GLP-1 peptide and an enhancer for use as a medicament by oral administration, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.

In some embodiments the present invention relates to a method of medical treatment comprising orally administering to a patient in need thereof a solid composition comprising a GLP-1 peptide and an enhancer, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.

The invention may also solve further problems that will be apparent from the disclosure of the exemplary embodiments.

The method or use of the invention comprises administration of a GLP-1 peptide, e.g. to a subject in need thereof. In some embodiments the GLP-1 peptide is administered in an amount in the range of 0.5-100 mg, such as in the range of 0.5-50 mg or 0.5-25 mg. In some embodiments the GLP-1 peptide is administered in an amount in the range of 1-25 mg or 5-50 mg. In some embodiments the GLP-1 peptide is administered in an amount in the range of 0.5-10 mg or 0.5-5 mg. In some embodiments the GLP-1 peptide is administered in a dosage which provides a steady state average plasma concentration of said peptide of 1-1000 nM, such as 1-300 nM or 10-100 nM.

DESCRIPTION

The present invention relates to methods (such as dosing regimens) of orally administering a GLP-1 peptide having a plasma half-life in humans of at least 60 hours or, in other words, to an improved use of said GLP-1 peptide in therapy for treatment of e.g. type 2 diabetes. The GLP-1 peptide may be administered in a solid dosage form, such as a tablet.

GLP-1 peptides with a plasma half-life in humans of at least 60 hours would have been expected to be preferred included in an oral dosing regimen with a low frequency of administration, e.g. once weekly administration; such dosing regimens are for example used for once weekly s.c. administration of the GLP-1 peptide semaglutide. For example, semaglutide can be administered by injection, such as s.c. injection, in the form of an aqueous composition comprising 1.34 mg/ml semaglutide, 1.42 mg/ml disodium hydrogen phosphate dihydrate, 14.0 mg/ml propylene glycol, 5.50 mg/ml phenol, pH 7.4; where pH is adjusted using hydrochloric acid and/or sodium hydroxide. Alternatively, semaglutide can be administered by injection, such as s.c. injection, in the form of an aqueous composition comprising 4.1 mg/ml semaglutide, 1.42 mg/ml disodium hydrogen phosphate dihydrate, 14.0 mg/ml propylene glycol, 5.50 mg/ml phenol, pH 7.4; where pH is adjusted using hydrochloric acid and/or sodium hydroxide.

However, it has by the inventors surprisingly been found that the variability in plasma concentration of a GLP-1 peptide is lower when dosing GLP-1 peptide according to methods or uses of the invention. The present invention may be seen as dosing regimens for oral administration of a GLP-1 peptide having a plasma half-life in humans of at least 60 hours comprising oral administration of said GLP-1 peptide more often than the half-life of said GLP-1 peptide would suggest, wherein said GLP-1 peptide may be administered in a solid dosage form, such as a tablet.

The following non-limiting example further illustrates one aspect of the invention: Once daily oral administration of a tablet comprising the GLP-1 peptide semaglutide provides surprisingly lower variability in the plasma concentration of said peptide when administered for a period of time (e.g. for a month) as compared to oral administration of said peptide using an alternative dosing regimen for the same period of time (e.g. a dosing regimen using once weekly administration). Examples 1-3 herein show that, surprisingly, daily oral administration of a tablet comprising a GLP-1 peptide provides reduced variability in plasma concentration. It is expected that a dosing regimen using once weekly administration of a GLP-1 peptide would result in variability in plasma concentration of the GLP-1 peptide in a similar range to that of a single dose administration.

When using a GLP-1 peptide according to a method or use of the invention, the variability in plasma concentration of the GLP-1 peptide is thus surprisingly lower when measuring the plasma concentration of the GLP-1 peptide after each dose to a population and comparing the measurements than when making similar measurements after an alternative dosing regimen.

In some embodiments the invention relates to certain oral dosing regimens of GLP-1 peptides which provide improvement in variability in plasma concentration of said GLP-1 peptide. In some embodiments the GLP-1 peptide is administered by a dosing regimen which provides an improved variability compared to administration following an alternative dosing regimen.

Reduction in the variability in plasma concentration and hence lower difference between minimum and maximum plasma concentrations in a population and/or in a patient would lead to less GLP-1 related side effects (such as nausea and vomiting) and better effect of the medical treatment (such as reduction in blood glucose and body weight).

In some embodiments the invention relates to a solid composition comprising a GLP-1 peptide and an enhancer for use as a medicament by oral administration, wherein said peptide has plasma half-life in humans of at least 60 hours, wherein said composition is administered at least 3 times, and wherein said composition is administered every second day or more often. In some embodiments the present invention relates to a method of medical treatment comprising orally administering to a patient in need thereof a solid composition comprising a GLP-1 peptide and an enhancer, wherein said peptide has plasma half-life in humans of at least 60 hours, wherein said composition is administered at least 3 times, and wherein said composition is administered every second day or more often.

In some embodiments the method or use of the invention comprises administration twice daily, once daily, or every second day. In some embodiments the method or use of the invention comprises administration at least every second day (i.e. administration every second day or more often), at least once daily, or at least twice daily.

The reduction in variation is not expected to occur until after a few administrations using the dosing regimen of the invention. Accordingly, in some embodiments the method or use of the invention is carried out for a period of time, such as administration at least 3 times. In some embodiments the method or use comprises administration at least 5 times or at least 7 times. In some embodiments the method or use comprises administration at least 10 times, at least 14 times or at least 21 times. In some embodiments the method or use is carried for a period of at least 2 weeks, at least 3 weeks, or at least 4 weeks.

The variability is evaluated by comparing the plasma concentration level (i.e. $C_{max}$, AUC or $C_{average}$) in a dosing interval (i.e. from one oral dosing to the next oral dosing). In some embodiments the term "variability" is herein, when used in connection with plasma concentration of a GLP-1 peptide, meant to mean the % CV in GLP-1 peptide plasma concentration level (i.e. $C_{max}$, AUC or $C_{average}$) in a dosing interval. In some embodiments the term "variability" is herein, when used in connection with plasma concentration of a GLP-1 peptide, meant to mean the % CV or % RSD in GLP-1 peptide plasma concentration level (i.e. $C_{max}$, AUC or $C_{average}$) after each dosing to a population.

In some embodiments the methods or uses of the invention are particularly suitable for orally administering a GLP-1 peptide for which the bioavailability is low. A low bioavailability may be a bioavailability of less than 10%. As used herein, the term "bioavailability" of a compound refers to the plasma concentration of said compound administered orally relative to the plasma concentration of the same amount of said compound administered intravenously.

In some embodiments the invention relates to a method or use of oral administration of a pharmaceutically active GLP-1 peptide to a subject, wherein said peptide has plasma half-life in humans of at least 60 hours, and wherein said method comprises the step of administering said peptide every second day or more often in a therapeutically effective amount. In some embodiments of the invention, the plasma half-life of the GLP-1 peptide in humans is about 70 hours, and said method comprises the step of administering said peptide every second day or more often in a therapeutically effective amount. In some embodiments the plasma half-life the GLP-1 peptide in humans is at least 100 hours, and said method comprises the step of administering said peptide every second day or more often in a therapeutically effective amount. In some embodiments the plasma half-life the GLP-1 peptide in humans is at least 120 hours, and said method comprises the step of administering said peptide every second day or more often in a therapeutically effective amount. In some embodiments the plasma half-life the GLP-1 peptide in humans is at least 160 hours, and said method comprises the step of administering said peptide every second day or more often in a therapeutically effective amount.

In some embodiments the invention relates to a GLP-1 peptide for use as an oral pharmaceutical every second day or more often in the treatment of diabetes, wherein said peptide has plasma half-life in humans of at least 60 hours. In some embodiments the invention relates to a GLP-1 peptide for use as an oral pharmaceutical every second day or more often in the treatment of diabetes, wherein said peptide has plasma half-life in humans of at least 70 hours. In some embodiments the invention relates to a GLP-1 peptide for use as an oral pharmaceutical every second day or more often in the treatment of diabetes, wherein said peptide has plasma half-life in humans of at least 100 hours. In some embodiments the invention relates to a GLP-1 peptide for use as an oral pharmaceutical every second day or more often in the treatment of diabetes, wherein said peptide has plasma half-life in humans of at least 120 hours. In some embodiments the invention relates to a GLP-1 peptide for use as an oral pharmaceutical every second day or more often in the treatment of diabetes, wherein said peptide has plasma half-life in humans of at least 160 hours.

By "plasma half-life" is herein meant the period of time it takes after administration (i.v. (intra venously) or p.o. (per os)) to halve the plasma concentration, measured after the initial distribution phase.

In some embodiments an "effective amount" of a GLP-1 peptide as used herein means an amount sufficient to cure, alleviate, or partially arrest the clinical manifestations of a given disease or state and its complications. An amount adequate to accomplish this is defined as "effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In some embodiments the term "treatment" or "treating" as used herein means the management and care of a patient for the purpose of combating a condition, such as a disease or a disorder. In some embodiments the term "treatment" or "treating" is intended to include the full spectrum of treatments for a given condition from which the patient is suffering, such as administration of the active GLP-1 peptide to alleviate the symptoms or complications; to delay the progression of the disease, disorder, or condition; to alleviate or relieve the symptoms and complications; and/or, to cure or eliminate the disease, disorder, or condition as well as to prevent the condition. In some embodiments prevention is to be understood as the management and care of a patient for the purpose of combating the disease, condition, or disorder and includes the administration of the active GLP-1 peptide to prevent the onset of the symptoms or complications.

In some embodiments the variability is less than 100%, i.e. the plasma concentration varies from one dosing to the next dosing by less than 100%. In some embodiments the variability in plasma concentration is 90% or less, alternatively 80% or less, alternatively 70% or less when comparing plasma concentration of GLP-1 from one dosing to the next dosing. In some embodiments the variability in plasma concentration is 60% or less, alternatively 50% or less, alternatively 40% or less when comparing plasma concentration of GLP-1 from one dosing to the next dosing. In some embodiments the variability is determined based on a population of at least 5 subjects, such as at least 10 subjects.

With the term "alternative dosing regimen" is herein meant a dosing regimen falling outside the claimed method. In some embodiments the term "alternative dosing regimen" as used herein is a dosing regimen (i.e. a method or use) comprising a dosing interval selected from the group consisting of a single administration, administration once weekly or less frequently, or administration every second week or less frequently.

In some embodiments the invention relates to a solid composition comprising a GLP-1 peptide and an enhancer for use as a medicament by oral administration, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1. In some embodiments the present invention relates to a method of medical treatment comprising orally administering to a patient in need thereof a solid composition comprising a GLP-1 peptide and an enhancer, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1.

In some embodiments the invention relates to a method or use of oral administration of a low clearance GLP-1 peptide is administered to a subject, wherein the ratio between the plasma half-life in days in humans of said peptide and the dosing interval in days of said peptide is 2:1 or more, such as 3:1 or more or 4:1 or more. 74. In some embodiments the ratio between the plasma half-life in days in humans of the GLP-1 peptide and the dosing interval in days of said peptide is more than 5:1 or more than 6:1. In some embodiments the ratio between the plasma half-life in days in humans of the GLP-1 peptide and the dosing interval in days of said peptide is more than 7:1 or more than 14:1. In some embodiments of the invention, a method or use of oral administration is described wherein a low clearance GLP-1 peptide in a therapeutically effective dosage is administered to a subject, wherein the ratio between the plasma half-life in days in humans of said peptide and the dosing interval in days of said peptide is 2:1 or more. Thus, when the plasma half-life of said GLP-1 peptide is e.g. 2 days in humans the dosing interval in days of said peptide is 1 or less, i.e. the peptide is dosed at least once per day; when the plasma half-life of said GLP-1 peptide is e.g. 4 days in humans the dosing interval in days of said peptide is 2 or less, i.e. the peptide is dosed at least once per 2 days; etc. In some embodiments the invention relates to a method or use of oral administration is described wherein a low clearance GLP-1 peptide in a therapeutically effective dosage is administered to a subject, wherein the ratio between the plasma half-life in days in humans of said peptide and the dosing interval in days of said peptide is 2:1 or more. In some embodiments the term "therapeutically effective dosage" refers to an administration comprising a therapeutically effective amount of GLP-1 peptide.

When used herein the term "low clearance GLP-1 peptide" or "low clearance GLP-1" shall mean a GLP-1 peptide which has a long plasma half-life in standard models of pharmacokinetics (e.g. pharmacokinetics in Beagle dogs, in pigs or in humans) compared to the GLP-1 peptide "liraglutide". In some embodiments the term "long plasma half-life" refers to a half-life which is longer than the half-life of liraglutide, wherein the half-life may be determined as described in the section herein with the title "Method for Determining Plasma Half-Life". In some embodiments the term "long plasma half-life" refers to a half-life in humans which is at least 60 hours, at least 70 hours, or at least 80 hours.

In some embodiments the method or use of oral administration of the invention results in reduced side effects relative to when using an alternative dosing regimen. In some embodiments the method of oral administration of the invention results in reduction in nausea and/or vomiting relative to when using an alternative dosing regimen. In some embodiments the method of oral administration of the invention results in reduction in nausea relative to when using an alternative dosing regimen. In some embodiments the method of oral administration of the invention results in reduction in vomiting relative to when using an alternative dosing regimen.

Method for Determining Plasma Half-Life

A pharmacokinetic study may be carried out to determine plasma half-life of the GLP-1 peptides after i.v. and/or p.o. administration to humans or animals (such as e.g. Beagle dogs). In some embodiments the plasma half-life of the GLP-1 peptide is determined in humans after i.v. administration. In some embodiments the plasma half-life of the GLP-1 peptide is determined in humans after p.o. administration.

In such study, subjects are typically administered a single dose i.v. or p.o. of the GLP-1 peptide in a relevant formulation. Blood samples are drawn at predefined time points after dosing, and samples are analysed for concentration of GLP-1 peptide with a relevant quantitative assay. Based on these measurements plasma concentration versus time profile are plotted and a so-called non-compartmental pharmacokinetic analysis of the data is performed.

For most active ingredients, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a plasma half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

The plasma concentration of GLP-1 peptides may be determined using any suitable method. The concentration in plasma of the GLP-1 peptides for the method or use of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO2009/030738 on p. 116-118. The plasma concentration of GLP-1 peptides may be determined using the LOCI method described herein in the experimental section titled "Analysis of Plasma Samples using LOCI". The plasma concentration of GLP-1 peptides may be determined using the LC-MS method described herein in the experimental section titled "Alternative Analysis of Plasma Samples using LC-MS".

Method for Determining Variability in Plasma Concentration

A pharmacokinetic study may be carried out to determine plasma half-life of the GLP-1 peptide after i.v. and/or p.o. administration to humans or animals (such as e.g. Beagle dogs). In such study, subjects are typically administered one or multiple doses p.o. of the GLP-1 peptide in a relevant formulation. Blood samples are drawn at predefined time points after dosing, and samples are analysed for concentration of active ingredient with a relevant quantitative assay. Based on these measurements plasma concentration versus time profile are plotted and a so-called non-compartmental pharmacokinetic analysis of the data is performed. The variability in plasma concentration can be determined as the % CV or % RSD for either $C_{max}$ or $C_{average}$ or AUC. For example, the variability in plasma concentration can be determined as the % CV for either $C_{max}$ or $C_{average}$ or AUC.

GLP-1 Peptide

The method or use of the present invention comprises a GLP-1 peptide with a plasma half-life in humans of at least 60 hours. The terms "GLP-1 peptide" and "active GLP-1 peptide" as used herein mean a peptide which is either human GLP-1 or an analogue or a derivative thereof with GLP-1 activity.

The term "human GLP-1" or "native GLP-1" as used herein means the human GLP-1 hormone whose structure and properties are well-known. Human GLP-1 is also denoted GLP-1(7-37), it has 31 amino acids and is the result from selective cleavage of the proglucagon molecule.

The GLP-1 peptides of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using a standard GLP-1 activity assay.

The term "GLP-1 analogue" as used herein means a modified human GLP-1 wherein one or more amino acid residues of human GLP-1 have been substituted by other amino acid residues and/or wherein one or more amino acid residues have been deleted from human GLP-1 and/or wherein one or more amino acid residues have been added and/or inserted to human GLP-1.

In some embodiments the GLP-1 peptide has plasma half-life in humans of at least 60 hours, such as at least about 70 hours, at least 90 hours, at least 100 hours, or such as at least 120 hours, at least 140 hours or at least 160 hours. In some embodiments the GLP-1 peptide has plasma half-life in humans of at least 60 hours, at least 70 hours or at least 90 hours. In some embodiments the GLP-1 peptide has plasma half-life in humans of at least 100 hours, or such as at least 120 hours, at least 140 hours or at least 160 hours. In some embodiments the GLP-1 peptide has plasma half-life in humans of at least 1 day, at least 36 hours or at least 2 days.

In some embodiments a GLP-1 analogue comprises 10 amino acid modifications (substitutions, deletions, additions (including insertions) and any combination thereof) or less relative to human GLP-1, alternatively 9, 8, 7, 6, 5, 4, 3 or 2 modifications or less, yet alternatively 1 modification relative to human GLP-1. In some embodiments a GLP-1 analogue comprises 5 amino acid modifications (substitutions, deletions, additions (including insertions) and any combination thereof) or less relative to human GLP-1.

Modifications in the GLP-1 molecule are denoted stating the position, and the one or three letter code for the amino acid residue substituting the native amino acid residue.

When using sequence listing, the first amino acid residue of a sequence is assigned no. 1. However, in what follows—according to established practice in the art for GLP-1 peptides—this first residue is referred to as no. 7, and subsequent amino acid residues are numbered accordingly, ending with no. 37. Therefore, generally, any reference herein to an amino acid residue number or a position number of the GLP-1(7-37) sequence is to the sequence starting with His at position 7 and ending with Gly at position 37. Using the one letter codes for amino acids, terms like 34E, 34Q, or 34R designates that the amino acid in the position 34 is E, Q and R, respectively. Using the three letter codes for amino acids, the corresponding expressions are 34Glu, 34Gln and 34Arg, respectively.

By "des7" or "(or Des$^7$)" is meant a native GLP-1 lacking the N-terminal amino acid, histidine. Thus, e.g., des7GLP-1(7-37) is an analogue of human GLP-1 where the amino acid in position 7 is deleted. This analogue may also be designated GLP-1(8-37). Similarly, (des7+des8); (des7, des8); (des7-8); or (Des$^7$, Des$^8$) in relation to an analogue of GLP-1(7-37), where the reference to GLP-1(7-37) may be implied, refers to an analogue in which the amino acids corresponding to the two N-terminal amino acids of native GLP-1, histidine and alanine, have been deleted. This analogue may also be designated GLP-1(9-37).

A non-limiting example of an analogue of the invention is [Aib$^8$,Arg$^{34}$]GLP-1(7-37), which designates a GLP-1(7-37) analogue, in which the alanine at position 8 has been substituted with α-aminoisobutyric acid (Aib) and the lysine at position 34 has been substituted with arginine. This analogue may also be designated (8Aib, R34) GLP-1(7-37).

The term "GLP-1 derivative" as used herein means a chemically modified parent GLP-1(7-37) or an analogue thereof, wherein the modification(s) are in the form of attachment of amides, carbohydrates, alkyl groups, acyl groups, esters, PEGylations, combinations thereof, and the like.

In some embodiments of the invention the modification(s) include attachment of a side chain to GLP-1(7-37) or an analogue thereof. In a particular aspect, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active peptide ingredient. Thus, the substituent, or side chain, as a whole is preferably referred to as an albumin binding moiety. In particular aspects, the side chain has at least 10 carbon atoms, or at least 12, 14, 16, 18, 20, 22, or at least 24 carbon atoms. In further particular aspects, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms. In some embodiments the GLP-1 peptide is an acylated GLP-1 peptide.

In some embodiments the albumin binding moiety comprises a portion which is particularly relevant for the albumin binding and thereby the protraction, which portion may accordingly be referred to as a "protracting moiety". The protracting moiety may be at, or near, the opposite end of the albumin binding moiety, relative to its point of attachment to the peptide.

In some embodiments the albumin binding moiety comprises a portion in between the protracting moiety and the point of attachment to the peptide, which portion may be referred to as a "linker", "linker moiety", "spacer", or the like. The linker may be optional, and hence in that case the albumin binding moiety may be identical to the protracting moiety.

In some embodiments the albumin binding moiety and/or the protracting moiety is lipophilic, and/or negatively charged at physiological pH (7.4).

The albumin binding moiety, the protracting moiety, or the linker may e.g. be covalently attached to a lysine residue of the GLP-1 peptide by acylation. In a preferred aspect, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

For the present purposes, the terms "albumin binding moiety", "protracting moiety", and "linker" may include the unreacted as well as the reacted forms of these molecules. Whether or not one or the other form is meant is clear from the context in which the term is used.

For the attachment to the GLP-1 peptide, the acid group of the fatty acid, or one of the acid groups of the fatty diacid, forms an amide bond with the epsilon amino group of a lysine residue in the GLP-1 peptide, preferably via a linker.

The term "fatty diacid" refers to fatty acids as defined above but with an additional carboxylic acid group in the omega position. Thus, fatty diacids are dicarboxylic acids.

Each of the two linkers of the derivative of the invention may comprise the following first linker element:

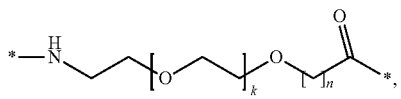

Chem I wherein k is an integer in the range of 1-5, and n is an integer in the range of 1-5.

In a particular aspect, when k=1 and n=1, this linker element may be designated OEG, or a di-radical of 8-amino-3,6-dioxaoctanic acid, and/or it may be represented by the following formula:

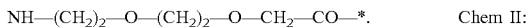

NH—(CH$_2$)$_2$—O—(CH$_2$)$_2$—O—CH$_2$—CO—*.     Chem II:

In another particular aspect, each linker of the derivative of the invention may further comprise, independently, a second linker element, preferably a Glu di-radical, such as Chem III and/or Chem IV:

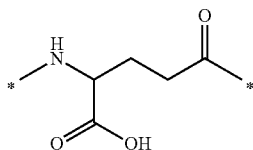

Chem III

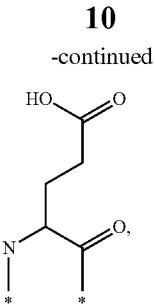

Chem IV wherein the Glu di-radical may be included p times, where p is an integer in the range of 1-3.

Chem III may also be referred to as gamma-Glu, or briefly γGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

Chem IV may also be referred to as alpha-Glu, or briefly aGlu, or simply Glu, due to the fact that it is the alpha carboxy group of the amino acid glutamic acid which is here used for connection to another linker element, or to the epsilon-amino group of lysine.

The above structures of Chem. III and Chem. IV cover the L-form, as well as the D-form of Glu. In particular aspects, Chem. III and/or Chem. IV is/are, independently, a) in the L-form, or b) in the D-form.

In still further particular aspects the linker has a) from 5 to 41 C-atoms; and/or b) from 4 to 28 hetero atoms.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118.

The conjugation of the GLP-1 analogue and the activated side chain is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate).

In some embodiments of the invention, the GLP-1 peptide is N-epsilon26-[2-(2-{2-[2-(2-{2-[(S)-4-Carboxy-4-(17-carboxyheptadecanoylamino)butyrylamino]ethoxy}ethoxy) acetyl-amino]ethoxy}ethoxy)acetyl][Aib8,Arg34]GLP-1-(7-37) (alternatively named N$^{6,26}$-{18-[N-(17-carboxyheptadecanoyl)-L-γ-glutamyl]-10-oxo-3,6,12,15- tetraoxa-9,18-diazaoctadecanoyl}-[8-(2-amino-2-propanoic acid),34-L-arginine] human glucagon-like peptide 1(7-37)) or $N^{\varepsilon 26}$ {2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl}, $N^{\varepsilon 37}$-{2-[2-(2-{2-[2-(2-{(S)-4-carboxy-4-[10-(4-carboxy-phenoxy) decanoylamino]butyrylamino}ethoxy)ethoxy]acetylamino}ethoxy)ethoxy]acetyl}-[Aib$^8$, Arg$^{34}$, Lys$^{37}$]GLP-1(7-37)-OH.

In some embodiments of the invention, the GLP-1 peptide is N-epsilon26-[2-(2-{2-[2-(2-{2-[(S)-4-Carboxy-4-(17-carboxyheptadecanoylamino)butyrylamino]ethoxy}ethoxy)acetyl-amino]ethoxy}ethoxy)acetyl][Aib8,Arg34]GLP-1-(7-37).

In some embodiments of the invention, the GLP-1 peptide is $N^{\varepsilon 26}${2-[2-(2-{2-[2-(2-{(S)-4-Carboxy-4-[10-(4-carboxyphenoxy)decanoylamino]butyrylamino}ethoxy)ethoxy]acetylamino}-ethoxy)ethoxy]acetyl}, $N^{\varepsilon 37}$-{2-[2-(2-{2-[2-(2-{(S)-4-carboxy-4-[10-(4-carboxyphenoxy)decanoyl-amino]butyrylamino}ethoxy)ethoxy]acetylamino}ethoxy)ethoxy]acetyl}-[Aib$^8$, Arg$^{34}$, Lys$^{37}$]GLP-1(7-37)-OH.

Enhancer

The method or use of the present invention may comprise an enhancer. In some embodiments the enhancer is water soluble. In some embodiments the term "enhancer" refers to a compound which increases the bioavailability of the GLP-1 peptide of the composition following oral administration. Accordingly, in some embodiments the enhancer is a bioavailability enhancer. In some embodiments the weight percentage of the enhancer is at least 60% (w/w), such as at least 70% (w/w) or at least 75% (w/w), of the total weight of the composition.

The enhancer may be a medium chain fatty acid or a salt thereof and has a carbon chain length of from about 4 to about 20 carbon atoms. In some embodiments the enhancer is a salt of capric acid, such as sodium caprate. In some embodiments the weight percentage of said medium chain fatty acid, such as a salt of capric acid (e.g. sodium caprate), is at least 60% (w/w), such as at least 70% (w/w) or at least 75% (w/w), of the total weight of the composition. In some embodiments the amount of said medium chain fatty acid, such as a salt of capric acid (e.g. sodium caprate), in the composition is at least 2.0 mmol, such as at least 2.5 mmol or at least 3.5 mmol, in one dosage unit. In some embodiments the amount of a salt of capric acid, such as sodium caprate, in the composition is at least 300 mg, at least 400 mg, or at least 500 mg.

In some embodiments the enhancer is a salt of N-(8-(2-hydroxybenzoyl)amino)caprylic acid. In some embodiments the enhancer is an absorption enhancer. The structural formula of N-(8-(2-hydroxybenzoyl)amino)caprylate is shown in formula (I).

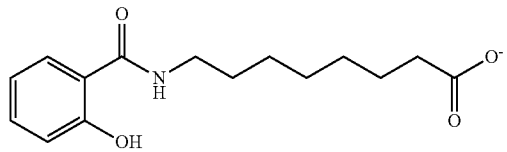

(I)

In some embodiments the salt of N-(8-(2-hydroxybenzoyl)amino)caprylic acid is in the caprylic acid form and/or the caprylate form. In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl) amino) caprylic acid is selected from the group consisting of the sodium salt, potassium salt and calcium salt of N-(8-(2-hydroxybenzoyl)amino)caprylic acid. Salts of N-(8-(2-hydroxybenzoyl)amino)caprylate may be prepared using the method described in e.g. WO96/030036, WO00/046182, WO01/092206 or WO2008/028859. The salt of N-(8-(2-hydroxybenzoyl)amino)caprylic acid may be crystalline and/or amorphous. In some embodiments the enhancer comprises the anhydrate, monohydrate, dihydrate, trihydrate, a solvate or one third of a hydrate of the salt of N-(8-(2-hydroxybenzoyl)amino) caprylic acid as well as combinations thereof. In some embodiments the enhancer is a salt of N-(8-(2-hydroxybenzoyl)amino)caprylic acid as described in WO2007/121318. In some embodiments the enhancer is sodium N-(8-(2-hydroxybenzoyl)amino)caprylate (referred to as "SNAC" herein), also known as sodium 8-(salicyloylamino) octanoate. In some embodiments the weight percentage of the salt of N-(8-(2-hydroxybenzoyl) amino)caprylic acid, such as SNAC, is at least 60% (w/w), such as at least 70% (w/w) or at least 75% (w/w), of the total weight of the composition. In some embodiments the weight percentage of the salt of N-(8-(2-hydroxybenzoyl)amino) caprylic acid, such as SNAC, is 50-90% (w/w) of the total weight of the composition. In some embodiments the amount of the salt of N-(8-(2-hydroxybenzoyl) amino) caprylic acid in the composition is in the range of 0.6-3.5 mmol. In some embodiments the amount of the salt of N-(8-(2-hydroxybenzoyl) amino)caprylic acid in the composition is at least 0.6 mmol. In some embodiments the amount of SNAC in the composition is in the range of 100-1000 mg. In some embodiments the amount of SNAC is 100-500 mg, such as 200-400 mg or 300 mg. In some embodiments the molar ratio between GLP-1 peptide and enhancer in the composition is less than 10, such as less than 5 or less than 1.

Composition

The method or use of the invention comprises a composition comprising a GLP-1 peptide and optionally an enhancer. In some embodiments the composition is in the form of a solid dosage form. In some embodiments the composition is in the form of a tablet. In some embodiments the composition is in the form of a capsule. In some embodiments the composition is in the form of a sachet. In some embodiments the composition comprises granules which have been manufactured by dry granulation. In some embodiments the composition comprises granules which have been manufactured by roller compaction. In some embodiments the moldings from the roller compaction process are comminuted into granules. In some embodiments the term "granulate" refers to one or more granules. In some embodiments the term "granule" refers to particles gathered into larger particles.

In some embodiments the term "composition" as used herein refers to one dosage unit.

In some embodiments the composition or granule comprises at least one pharmaceutically acceptable excipient. The term "excipient" as used herein broadly refers to any component other than the active therapeutic ingredient(s). The excipient may be an inert substance, which is inert in the sense that it substantially does not have any therapeutic and/or prophylactic effect per se. The excipient may serve various purposes, e.g. as a enhancer, absorption enhancer, vehicle, filler (also known as diluents), binder, lubricant, glidant, disintegrant, crystallization retarders, acidifying agent, alkalizing agent, preservative, antioxidant, buffering agent, chelating agent, complexing agents, surfactant agent, emulsifying and/or solubilizing agents, sweetening agents, wetting agents stabilizing agent, colouring agent, flavouring agent, and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In some embodiments the composition or granule comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101.

In some embodiments the composition or granule comprises a binder, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, L-hydroxypropylcellulose (low-substituted), hypromellose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as povidone K 90.

In some embodiments the composition or granule comprises a disintegrant, such as alginic acid, alginates, microcrystalline cellulose, hydroxypropyl cellulose, other cellulose derivatives, croscarmellose sodium, crospovidone, polacrillin potassium, sodium starch glycolate, starch, pregelatinized starch, or carboxymethyl starch (e.g. Primogel® and Explotab®).

In some embodiments the composition or granule comprises a lubricant, such as stearic acid, magnesium stearate, calcium stearate or other metallic stearate, talc, waxes, glycerides, light mineral oil, glyceryl behenate, hydrogenated vegetable oils, glyceryl stearyl fumarate, polyethylene glycols, alkyl sulfates, or sodium benzoate. In some embodiments the composition or granule comprises a lubricant, such as magnesium silicate, talc, or colloidal silica. In some embodiments the lubricant is magnesium stearate.

In some embodiments the composition or granule comprises one or more excipients selected from crystallization retarders, such as Povidone, etc.; solubilizing agents (also known as surfactants), such as anionic surfactants (e.g. Pluronic or Povidone), cationic surfactants, nonionic surfactants, and/or zwitterionic surfactants; colouring agents, including dyes and pigments, such as Iron Oxide Red or Yellow, titanium dioxide, and/or talc; and/or pH control agents, such as citric acid, tartaric acid, fumaric acid, sodium citrate, dibasic calcium phosphate, and/or dibasic sodium phosphate.

In some embodiments the composition comprises at least 60% (w/w) enhancer, less than 10% (w/w) binder, 5-40% (w/w) filler, and less than 10% (w/w) lubricant. In some embodiments the enhancer is a salt of N-(8-(2-hydroxybenzoyl)amino)caprylic acid and the composition comprises a first granule comprising GLP-1 peptide and no a salt of N-(8-(2-hydroxybenzoyl)amino)caprylic acid and a second granule comprising a salt of N-(8-(2-hydroxybenzoyl)amino)caprylic acid and no GLP-1 peptide.

In some embodiments the weight of the tablet is in the range of 150 mg to 1000 mg, such as in the range of 300-600 mg or such as 300-500 mg.

The composition may comprise one or more coatings, which may be prepared according to methods well known in the art.

Methods of Preparation of Compositions

The composition for use in the present invention may be prepared as is known in the art. In some embodiments the composition may be granulated prior to being compressed into tablets. In some embodiments the granules of the invention are manufactured by dry granulation, such as by roller compaction compaction. In some embodiments the moldings from the roller compactions process are comminuted into granules. The composition may comprise one or more intragranular parts and an extragranular part, wherein the intragranular parts have been granulated, and wherein the extragranular part has been added after granulation. A first intragranular part may comprise the GLP-1 peptide and one or more excipients, and a second intragranular part may comprise the enhancer and optionally one or more excipients. A first intragranular part may comprise the GLP-1 peptide, filler and/or a binder and a second intragranular part may comprise the enhancer, lubricant and/or filler. In some embodiments the first intragranular part comprises the GLP-1 peptide, microcrystalline cellulose and/or povidone and the second intragranular part comprises the enhancer, magnesium stearate and/or microcrystalline cellulose. The extragranular part may comprise a lubricant. In some embodiments the extragranular part comprises magnesium stearate.

To prepare a dry blend of tabletting material, the various components are weighed, optionally delumped and then combined. The mixing of the components may be carried out until a homogeneous blend is obtained.

In some embodiments at least a part of the composition is dry granulated or wet granulated. A granulate may be produced in a manner known to a person skilled in the art, for example by dry granulation techniques in which the pharmaceutically active agent and/or enhancers are compacted with the excipients to form relatively large moldings, for example slugs or ribbons, which are comminuted by grinding, and the ground material serves as the tabletting material to be later compressed into tablets. Suitable equipment for dry granulation includes but is not limited to roller compaction equipment from Gerteis, such as Gerteis MINI-PACTOR. In some embodiments the granulate is prepared by roller compaction. In some embodiments the moldings from the roller compactions process are comminuted into granules. Alternatively, a granulate can be obtained by wet granulation which may be carried out by mixing the pharmaceutically active agent dissolved in water with a dry blend of the enhancers and optionally one or more excipients followed by drying of the granulate.

To compress the tabletting material into a solid oral dosage form, for example a tablet, a tablet press may be used. In a tabletting press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom). In some embodiments the tablet is prepared by exerting a compression force in the range of 5-25 kN.

Indications

The composition for use in the present invention is for use in as a medicament. In some embodiments the composition is for use in the treatment or prevention of diabetes and/or obesity.

It will be appreciated that the composition or the GLP-1 peptide for use as an oral pharmaceutical (i.e. medicament), may be described as a method of administration or alternatively be described as use of a composition in the manufacture of an oral pharmaceutical. It will be appreciated that the method of administration described herein may alternatively be described as a composition for use as an oral pharmaceutical, alternatively use of a composition in the manufacture of an oral pharmaceutical. The method of administration described herein may alternatively be described as a GLP-1 peptide for use as an oral pharmaceutical, alternatively use of a GLP-1 peptide in the manufacture of an oral pharmaceutical. Analogously, the use of a GLP-1 peptide described herein may alternatively be described as a method of administration or use of a GLP-1 peptide in the manufacture of an oral pharmaceutical. In some embodiments the terms "dosing regimen" and "method of administration" are used interchangeably herein. Herein, in some embodiments the term "use" includes a composition for use, e.g. "use in medicine" includes a "composition for use in medicine". In some embodiments the term "method" as used herein includes a method of administration, e.g. a method of oral administration.

The method of administration of the invention comprises oral therapy. In some embodiments the method comprises treatment or prevention of diabetes and/or obesity.

In some embodiments the method or use comprises (e.g. the GLP-1 peptide of the invention may be used for the following medical treatments):

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

In some embodiments the indication is (i). In some embodiments the indication is (ii). In a still further particular aspect the indication is (iii). In some embodiments the indication is type 2 diabetes and/or obesity.

In some embodiments the method or use comprises prevention, treatment, reduction and/or induction in one or more diseases or conditions defined herein. In some embodiments the indication is (i) and (iii). In some embodiments the indication is (ii) and (iii). In some embodiments the method comprises prevention, treatment, reduction and/or induction in one or more diseases or conditions selected from a) and b), a) and c), b) and c), or a), b) and c) as defined in claim 1.

In some embodiments the invention comprises administration of an effective amount of a GLP-1 peptide. In some embodiments the invention relates to administration of an effective amount of a GLP-1 peptide.

In some embodiments, as used herein, specific values given in relation to numbers or intervals may be understood as the specific value or as about the specific value.

EMBODIMENTS OF THE INVENTION

The following are non-limiting embodiments of the invention:

1. A solid composition comprising a GLP-1 peptide and an enhancer for use as a medicament by oral administration, wherein said peptide has plasma half-life in humans of at least 60 hours, wherein said composition is administered at least 3 times, and wherein
   a) said composition is administered every second day or more often; or
   b) said composition is administered such that the ratio between the plasma half-life in days in humans of said peptide and the dosing interval in days of said composition is more than 2:1.
2. The composition according to any one of the preceding embodiments, wherein said composition is in the form of a tablet.
3. The composition according to any one of the preceding embodiments, wherein said composition is administered twice daily, once daily, or every second day.
4. The composition according to any one of the preceding embodiments, wherein said peptide is administered at least every second day.
5. The composition according to any one of the preceding embodiments, wherein said peptide is administered at least once daily.
6. The composition according to any one of the preceding embodiments, wherein said peptide is administered at least twice daily.
7. The composition according to any one of the preceding embodiments, wherein said peptide is a GLP-1 peptide.

8. The composition according to any one of the preceding embodiments, wherein said peptide is an acylated GLP-1 peptide.
9. The composition according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37) or $N^{\varepsilon 26}$ {2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl}, $N^{\varepsilon 37}$-{2-[2-(2-{2-[2-(2-{(S)-4-carboxy-4-[10-(4-carboxy-phenoxy)decanoylamino]butyrylamino}ethoxy)ethoxy]acetylamino}ethoxy)ethoxy]acetyl}-[Aib$^8$, Arg$^{34}$,Lys$^{37}$]GLP-1(7-37)-OH.
10. The composition according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37).
11. The composition according to any one of the preceding embodiments, wherein said peptide is $N^{\varepsilon 26}$ {2-[2-(2-{2-[2-(2-{(S)-4-Carboxy-4-[10-(4-carboxyphenoxy)decanoylamino]butyrylamino}-ethoxy)ethoxy]acetylamino}ethoxy)ethoxy]acetyl}, $N^{\varepsilon 37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib$^8$, Arg$^{34}$,Lys$^{37}$]GLP-1(7-37)-OH.
12. The composition according to any one of the preceding embodiments, wherein said peptide is administered in a composition further comprising one or more pharmaceutically acceptable excipients.
13. The composition according to any one of the preceding embodiments, wherein said composition is in the form a tablet or a capsule.
14. The composition according to any one of the preceding embodiments, wherein said peptide is administered in a dosage which provides a steady state average plasma concentration of said peptide of 1-1000 nM.
15. A GLP-1 according to any one of the preceding embodiments, wherein said peptide is administered in a dosage which provides a steady state average plasma concentration of said peptide of 1-300 nM.
16. A GLP-1 according to any one of the preceding embodiments, wherein said peptide is administered in a dosage which provides a steady state average plasma concentration of said peptide of 10-100 nM.
17. The composition according to any one of the preceding embodiments, wherein said treatment comprises prevention and/or treatment of type 2 diabetes or obesity.
18. The composition according to any one of the preceding embodiments, wherein said enhancer is a salt of N-(8-(2-hydroxybenzoyl)amino)caprylic acid, such as SNAC.
19. The composition according to any one of the preceding embodiments, wherein the weight percentage of a salt of N-(8-(2-hydroxybenzoyl)amino)caprylic acid, such as SNAC, is at least 50% (w/w) of said composition.
20. The composition according to any one of the preceding embodiments, wherein the amount of SNAC is 100-500 mg SNAC, such as 200-400 mg or 300 mg SNAC.
21. The composition according to any one of the preceding embodiments, wherein said enhancer is a salt of capric acid, such as sodium caprate.
22. The composition according to any one of the preceding embodiments, wherein the amount of said salt of capric acid, such as sodium caprate, is at least 300 mg.
23. The composition according to any one of the preceding embodiments, wherein the weight percentage of said salt of capric acid, such as sodium caprate, is at least 50% (w/w) of said composition.
24. The composition according to any one of the preceding embodiments, wherein said composition comprises a coating.
25. The composition according to any one of the preceding embodiments, wherein said peptide has plasma half-life in humans of at least 70 hours.
26. The composition according to any one of the preceding embodiments, wherein said peptide is administered in an amount of 0.01-100 mg, such as 2-60 mg, or such as such as at least 5 mg or at least 10 mg.
27. The composition according to any one of the preceding embodiments, wherein said peptide is administered in an amount in the range of 0.5-100 mg.
28. The composition according to any one of the preceding embodiments, wherein said peptide is administered in an amount in the range of 0.5-50 mg.
29. The composition according to any one of the preceding embodiments, wherein said peptide is administered in an amount in the range of 0.5-25 mg.
30. The composition according to any one of the preceding embodiments, wherein said peptide is administered in an amount in the range of 1-25 mg.
31. The composition according to any one of the preceding embodiments, wherein said peptide is administered in an amount in the range of 5-50 mg.
32. The composition according to any one of the preceding embodiments, wherein said peptide is administered in an amount in the range of 0.5-10 mg.
33. The composition according to any one of the preceding embodiments, wherein said peptide is administered in an amount in the range of 0.5-5 mg.
34. The composition according to any one of the preceding embodiments, wherein said composition comprises 1-100 mg GLP-1 peptide and 100-500 mg or 50-90% (w/w) SNAC.
35. The composition according to any one of the preceding embodiments, wherein said peptide is semaglutide.
36. The composition according to any one of the preceding embodiments, wherein said composition comprises 1-100 mg semaglutide and 100-500 mg or 50-90% (w/w) SNAC.
37. The composition according to any one of the preceding embodiments, wherein said composition comprises 2-40 mg semaglutide and 200-400 mg (such as 300 mg) or 50-90% (w/w) SNAC.
38. The composition according to any one of the preceding embodiments, wherein said peptide is comprised in a pharmaceutical composition further comprising one or more pharmaceutically acceptable excipients.
39. The composition according to any one of the preceding embodiments, wherein said composition comprises GLP-1 peptide, SNAC, microcrystalline cellulose, povidone, and magnesium stearate.
40. The composition according to any one of the preceding embodiments, wherein said composition comprises 1-100 mg GLP-1 peptide, 100-500 mg SNAC, microcrystalline cellulose, povidone, and magnesium stearate.
41. The composition according to any one of the preceding embodiments, wherein said composition comprises 1-100 mg GLP-1 peptide, 50-90% (w/w) SNAC, microcrystalline cellulose, povidone, and magnesium stearate.
44. The composition according to any one of the preceding embodiments, wherein said composition contains 1-100 mg GLP-1 peptide, 100-500 mg or 50-90% (w/w) SNAC, microcrystalline cellulose, povidone, and magnesium stearate.
45. The composition according to any one of the preceding embodiments, wherein said composition contains 1-100 mg GLP-1 peptide, 100-500 mg or 50-90% (w/w) SNAC, microcrystalline cellulose, povidone, and magnesium stearate.
46. The composition according to any one of the preceding embodiments, wherein said composition contains 1-100 mg GLP-1 peptide, 200-400 mg (such as 300 mg) or 50-90% (w/w) SNAC, microcrystalline cellulose, povidone, and magnesium stearate.
47. The composition according to any one of the preceding embodiments, wherein said composition contains 1-100 mg semaglutide, 200-400 mg (such as 300 mg) or 50-90% (w/w) SNAC, microcrystalline cellulose, povidone, and magnesium stearate.
48. The composition according to any one of the preceding embodiments, wherein said composition contains 2-60 mg semaglutide, 200-400 mg (such as 300 mg) or 50-90% (w/w) SNAC, microcrystalline cellulose, povidone, and magnesium stearate.
49. The composition according to any one of the preceding embodiments, wherein said composition contains 5-40 mg semaglutide, 200-400 mg (such as 300 mg) or 50-90% (w/w) SNAC, microcrystalline cellulose, povidone, and magnesium stearate.
50. The composition according to any one of the preceding embodiments, wherein said composition is administered at least 5 times, such as at least 7 times or at least 10 times.
51. The composition according to any one of the preceding embodiments, wherein said composition is administered at least 14 times or at least 21 times.
52. The composition according to any one of the preceding embodiments, wherein said composition is administered for at least 2 weeks, for at least 3 weeks, or for at least 4 weeks.
53. The composition according to any one of the preceding embodiments, wherein the ratio between the plasma half-life in days in humans of said peptide and the dosing interval in days of said peptide is more than 3:1.
54. The composition according to any one of the preceding embodiments, wherein the ratio between the plasma half-life in days in humans of said peptide and the dosing interval in days of said peptide is more than 4:1.
55. The composition according to any one of the preceding embodiments, wherein the ratio between the plasma half-life in days in humans of said peptide and the dosing interval in days of said peptide is more than 5:1.
56. The composition according to any one of the preceding embodiments, wherein the ratio between the plasma half-life in days in humans of said peptide and the dosing interval in days of said peptide is more than 6:1.
57. The composition according to any one of the preceding embodiments, wherein the ratio between the plasma half-life in days in humans of said peptide and the dosing interval in days of said peptide is more than 7:1.
58. The composition according to any one of the preceding embodiments, wherein the ratio between the plasma half-life in days in humans of said peptide and the dosing interval in days of said peptide is more than 14:1.
59. The composition according to any one of the preceding embodiments, wherein plasma half-life is measured after i.v. administration.
60. The composition according to any one of the preceding embodiments, wherein plasma half-life is measured after p.o. administration.
61. The composition according to any one of the preceding embodiments, wherein said composition is for use in the treatment or prevention of diabetes and/or obesity.
62. The composition according to any one of the preceding embodiments, wherein said composition is for use in the following medical treatments:
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;
(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes; and/or
(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.
63. A method of oral administration of a pharmaceutically active GLP-1 peptide to a subject, wherein said peptide has plasma half-life in humans of at least 60 hours, and wherein said method comprises the step of administering said peptide every second day or more often in a therapeutically effective amount.
64. A method of oral administration of a solid composition comprising a GLP-1 peptide and an enhancer to a subject in need thereof, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.
65. A method of oral administration of a solid composition comprising a GLP-1 peptide and an enhancer to a subject in need thereof, wherein said peptide has plasma half-life in humans of at least 60 hours, wherein said composition is administered at least 3 times, and wherein said composition is administered every second day or more often.
66. A method of oral administration of a solid composition comprising a GLP-1 peptide and an enhancer to a subject in need thereof, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1.
67. The method according to any one of the preceding embodiments, wherein said composition is in the form of a tablet.
68. The method according to any one of the preceding embodiments, wherein said composition is administered twice daily, once daily, or every second day.
69. The method according to any one of the preceding embodiments, wherein said peptide is administered at least every second day.

70. The method according to any one of the preceding embodiments, wherein said peptide is administered at least once daily.
71. The method according to any one of the preceding embodiments, wherein said peptide is administered at least twice daily.
72. The method according to any one of the preceding embodiments, wherein said peptide is a GLP-1 peptide.
73. The method according to any one of the preceding embodiments, wherein said peptide is an acylated GLP-1 peptide.
74. The method according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37) or $N^{\varepsilon 26}$\{2-[2-(2-\{2-[2-(2-\{(S)-4-Carboxy-4-[10-(4-carboxyphenoxy)decanoylamino]butyrylamino\}ethoxy)ethoxy]acetylamino\}ethoxy)ethoxy]acetyl\}, $N^{\varepsilon 37}$-\{2-[2-(2-\{2-[2-(2-\{(S)-4-carboxy-4-[10-(4-carboxy-phenoxy)decanoylamino]butyrylamino\}ethoxy)ethoxy]acetylamino\}ethoxy)ethoxy]acetyl\}[Aib$^8$, Arg$^{34}$,Lys$^{37}$]GLP-1(7-37)-OH.
75. The method according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37).
11. The method according to any one of the preceding embodiments, wherein said peptide is $N^{\varepsilon 26}$\{2-[2-(2-\{2-[2-(2-\{(S)-4-Carboxy-4-[10-(4-carboxyphenoxy)decanoylamino]butyrylamino\}ethoxy)ethoxy]acetylamino\}ethoxy)ethoxy]acetyl\}, $N^{\varepsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$^8$, Arg$^{34}$,Lys$^{37}$]GLP-1(7-37)-OH.
76. The method according to any one of the preceding embodiments, wherein said peptide is administered in a composition further comprising one or more pharmaceutically acceptable excipients.
77. The method according to any one of the preceding embodiments, wherein said composition is in the form a tablet or a capsule.
78. The method according to any one of the preceding embodiments, wherein said peptide is administered in a dosage which provides a steady state average plasma concentration of said peptide of 1-1000 nM.
79. A GLP-1 according to any one of the preceding embodiments, wherein said peptide is administered in a dosage which provides a steady state average plasma concentration of said peptide of 1-300 nM.
80. A GLP-1 according to any one of the preceding embodiments, wherein said peptide is administered in a dosage which provides a steady state average plasma concentration of said peptide of 10-100 nM.
81. The method according to any one of the preceding embodiments, wherein said treatment comprises prevention and/or treatment of type 2 diabetes or obesity.
82. The method according to any one of the preceding embodiments, wherein said enhancer is a salt of N-(8-(2-hydroxybenzoyl)amino)caprylic acid, such as SNAC.
83. The method according to any one of the preceding embodiments, wherein the weight percentage of a salt of N-(8-(2-hydroxybenzoyl)amino)caprylic acid, such as SNAC, is at least 50% (w/w) of said composition.
84. The method according to any one of the preceding embodiments, wherein the amount of SNAC is 100-500 mg SNAC, such as 200-400 mg or 300 mg SNAC.
85. The method according to any one of the preceding embodiments, wherein said enhancer is a salt of capric acid, such as sodium caprate.
86. The method according to any one of the preceding embodiments, wherein the amount of said salt of capric acid, such as sodium caprate, is at least 300 mg.
87. The method according to any one of the preceding embodiments, wherein the weight percentage of said salt of capric acid, such as sodium caprate, is at least 50% (w/w) of said composition.
88. The method according to any one of the preceding embodiments, wherein said composition comprises a coating.
89. The method according to any one of the preceding embodiments, wherein said peptide has plasma half-life in humans of at least 70 hours.
90. The method according to any one of the preceding embodiments, wherein said peptide is administered in an amount of 0.01-100 mg, such as 2-60 mg, or such as such as at least 5 mg or at least 10 mg.
91. The method according to any one of the preceding embodiments, wherein said peptide is administered in an amount in the range of 0.5-100 mg.
92. The method according to any one of the preceding embodiments, wherein said peptide is administered in an amount in the range of 0.5-50 mg.
93. The method according to any one of the preceding embodiments, wherein said peptide is administered in an amount in the range of 0.5-25 mg.
94. The method according to any one of the preceding embodiments, wherein said peptide is administered in an amount in the range of 1-25 mg.
95. The method according to any one of the preceding embodiments, wherein said peptide is administered in an amount in the range of 5-50 mg.
96. The method according to any one of the preceding embodiments, wherein said peptide is administered in an amount in the range of 0.5-10 mg.
97. The method according to any one of the preceding embodiments, wherein said peptide is administered in an amount in the range of 0.5-5 mg.
98. The method according to any one of the preceding embodiments, wherein said composition comprises 1-100 mg GLP-1 peptide and 100-500 mg or 50-90% (w/w) SNAC.
99. The method according to any one of the preceding embodiments, wherein said peptide is semaglutide.
100. The method according to any one of the preceding embodiments, wherein said composition comprises 1-100 mg semaglutide and 100-500 mg or 50-90% (w/w) SNAC.
101. The method according to any one of the preceding embodiments, wherein said composition comprises 2-40 mg semaglutide and 200-400 mg (such as 300 mg) or 50-90% (w/w) SNAC.
102. The method according to any one of the preceding embodiments, wherein said peptide is comprised in a pharmaceutical composition further comprising one or more pharmaceutically acceptable excipients.
103. The method according to any one of the preceding embodiments, wherein said composition comprises GLP-1 peptide, SNAC, microcrystalline cellulose, povidone, and magnesium stearate.

104. The method according to any one of the preceding embodiments, wherein said composition comprises 1-100 mg GLP-1 peptide, 100-500 mg SNAC, microcrystalline cellulose, povidone, and magnesium stearate.
105. The method according to any one of the preceding embodiments, wherein said composition comprises 1-100 mg GLP-1 peptide, 50-90% (w/w) SNAC, microcrystalline cellulose, povidone, and magnesium stearate.
106. The method according to any one of the preceding embodiments, wherein said composition contains 1-100 mg GLP-1 peptide, 100-500 mg or 50-90% (w/w) SNAC, microcrystalline cellulose, povidone, and magnesium stearate.
107. The method according to any one of the preceding embodiments, wherein said composition contains 1-100 mg GLP-1 peptide, 100-500 mg or 50-90% (w/w) SNAC, microcrystalline cellulose, povidone, and magnesium stearate.
108. The method according to any one of the preceding embodiments, wherein said composition contains 1-100 mg GLP-1 peptide, 200-400 mg (such as 300 mg) or 50-90% (w/w) SNAC, microcrystalline cellulose, povidone, and magnesium stearate.
109. The method according to any one of the preceding embodiments, wherein said composition contains 1-100 mg semaglutide, 200-400 mg (such as 300 mg) or 50-90% (w/w) SNAC, microcrystalline cellulose, povidone, and magnesium stearate.
110. The method according to any one of the preceding embodiments, wherein said composition contains 2-60 mg semaglutide, 200-400 mg (such as 300 mg) or 50-90% (w/w) SNAC, microcrystalline cellulose, povidone, and magnesium stearate.
111. The method according to any one of the preceding embodiments, wherein said composition contains 5-40 mg semaglutide, 200-400 mg (such as 300 mg) or 50-90% (w/w) SNAC, microcrystalline cellulose, povidone, and magnesium stearate.
112. The method according to any one of the preceding embodiments, wherein said composition is administered at least 5 times, such as at least 7 times or at least 10 times.
113. The method according to any one of the preceding embodiments, wherein said composition is administered at least 14 times or at least 21 times.
114. The method according to any one of the preceding embodiments, wherein said composition is administered for at least 2 weeks, for at least 3 weeks, or for at least 4 weeks.
115. The method according to any one of the preceding embodiments, wherein the ratio between the plasma half-life in days in humans of said peptide and the dosing interval in days of said peptide is more than 3:1.
116. The method according to any one of the preceding embodiments, wherein the ratio between the plasma half-life in days in humans of said peptide and the dosing interval in days of said peptide is more than 4:1.
117. The method according to any one of the preceding embodiments, wherein the ratio between the plasma half-life in days in humans of said peptide and the dosing interval in days of said peptide is more than 5:1.
118. The method according to any one of the preceding embodiments, wherein the ratio between the plasma half-life in days in humans of said peptide and the dosing interval in days of said peptide is more than 6:1.
119. The method according to any one of the preceding embodiments, wherein the ratio between the plasma half-life in days in humans of said peptide and the dosing interval in days of said peptide is more than 7:1.
120. The method according to any one of the preceding embodiments, wherein the ratio between the plasma half-life in days in humans of said peptide and the dosing interval in days of said peptide is more than 14:1.
121. The method according to any one of the preceding embodiments, wherein plasma half-life is measured after i.v. administration.
122. The method according to any one of the preceding embodiments, wherein plasma half-life is measured after p.o. administration.
123. The method according to any one of the preceding embodiments, wherein said composition is for use in the treatment or prevention of diabetes and/or obesity.
124. The method according to any one of the preceding embodiments, wherein said composition is for use in the following medical treatments:
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;
(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes; and/or
(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.
125. Use of a GLP-1 peptide in the manufacture of a medicament for oral administration in the treatment of a disease or condition, such as diabetes, wherein said peptide has plasma half-life in humans of at least 60 hours, wherein said composition is administered at least 3 times, and a) said composition is administered every second day or more often; or b) said composition is administered such that the ratio between the plasma half-life in days in humans of said peptide and the dosing interval in days of said composition is more than 2:1.
126. Use of a solid composition comprising a GLP-1 peptide and an enhancer in the manufacture of a medicament for oral administration in the treatment of a disease or condition, such as diabetes, wherein said peptide has plasma half-life in humans of at least 60 hours, wherein said composition is administered at least 3 times, and wherein said composition is administered every second day or more often.
127. Use of a solid composition comprising a GLP-1 peptide and an enhancer in the manufacture of a medicament for oral administration in the treatment of a disease or condition, such as diabetes, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1.
128. The use according to any one of embodiments 125-127, wherein said GLP-1 peptide and/or said composition is as defined in any combination of the previous embodiments.

Further Particular Embodiments

The following are particular non-limiting embodiments of the invention:

1. A GLP-1 peptide for use as an oral pharmaceutical every second day or more often in medical treatment, wherein said peptide has plasma half-life in humans of at least 60 hours.
2. A GLP-1 peptide which is a low clearance GLP-1 peptide for use as an oral pharmaceutical in medical treatment, wherein dosing regimen is such that the ratio between the plasma half-life in days in humans of said peptide and the dosing interval in days of said peptide is more than 2:1.
3. A GLP-1 peptide according to any one of the preceding embodiments, wherein the ratio between the plasma half-life in days in humans of said peptide and the dosing interval in days of said peptide is more than 3:1.
4. A GLP-1 peptide according to any one of the preceding embodiments, wherein the ratio between the plasma half-life in days in humans of said peptide and the dosing interval in days of said peptide is more than 4:1.
5. A GLP-1 peptide according to any one of the preceding embodiments, wherein the ratio between the plasma half-life in days in humans of said peptide and the dosing interval in days of said peptide is more than 5:1.
6. A GLP-1 peptide according to any one of the preceding embodiments, wherein the ratio between the plasma half-life in days in humans of said peptide and the dosing interval in days of said peptide is more than 6:1.
7. A GLP-1 peptide according to any one of the preceding embodiments, wherein the ratio between the plasma half-life in days in humans of said peptide and the dosing interval in days of said peptide is more than 7:1.
8. A GLP-1 peptide according to any one of the preceding embodiments, wherein the ratio between the plasma half-life in days in humans of said peptide and the dosing interval in days of said peptide is more than 14:1.
9. A GLP-1 peptide according to any one of the preceding embodiments, wherein plasma half-life is measured after i.v. administration.
10. A GLP-1 peptide according to any one of the preceding embodiments, wherein plasma half-life is measured after p.o. administration.
11. A GLP-1 peptide according to any one of the preceding embodiments, wherein said peptide has plasma half-life in humans of at least 1 day.
12. A GLP-1 peptide according to any one of the preceding embodiments, wherein said peptide has plasma half-life in humans of at least 36 hours.
13. A GLP-1 peptide according to any one of the preceding embodiments, wherein said peptide has plasma half-life in humans of at least 2 days.
14. A GLP-1 peptide according to any one of the preceding embodiments, wherein said peptide has plasma half-life in humans of at least 60 hours.
15. A GLP-1 peptide according to any one of the preceding embodiments, wherein said peptide is administered at least every second day.
16. A GLP-1 peptide according to any one of the preceding embodiments, wherein said peptide is administered at least once daily.
17. A GLP-1 peptide according to any one of the preceding embodiments, wherein said peptide is administered at least twice daily.
18. A GLP-1 peptide according to any one of the preceding embodiments, wherein said peptide is administered in an amount in the range of 0.5-100 mg.
19. A GLP-1 peptide according to any one of the preceding embodiments, wherein said peptide is administered in an amount in the range of 0.5-50 mg.
20. A GLP-1 peptide according to any one of the preceding embodiments, wherein said peptide is administered in an amount in the range of 0.5-25 mg.
21. A GLP-1 peptide according to any one of the preceding embodiments, wherein said peptide is administered in an amount in the range of 1-25 mg.
22. A GLP-1 peptide according to any one of the preceding embodiments, wherein said peptide is administered in an amount in the range of 5-50 mg.
23. A GLP-1 peptide according to any one of the preceding embodiments, wherein said peptide is administered in an amount in the range of 0.5-10 mg.
24. A GLP-1 peptide according to any one of the preceding embodiments, wherein said peptide is administered in an amount in the range of 0.5-5 mg.
25. A GLP-1 peptide according to any one of the preceding embodiments, wherein said peptide is a GLP-1 peptide.
26. A GLP-1 peptide according to any one of the preceding embodiments, wherein said peptide is an acylated GLP-1 peptide.
27. A GLP-1 peptide according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8, Arg34]GLP-1-(7-37) or $N^{\varepsilon 26}$\{2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl\}, $N^{\varepsilon 37}$-\{2-[2-(2-{2-[2-(2-{(S)-4-carboxy-4-[10-(4-carboxy-phenoxy)decanoylamino]butyrylamino}ethoxy)ethoxy]acetylamino}ethoxy)ethoxy]acetyl\}-[Aib$^8$, Arg$^{34}$,Lys$^{37}$]GLP-1(7-37)-OH.
28. A GLP-1 peptide according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37).
29. A GLP-1 peptide according to any one of the preceding embodiments, wherein said peptide is $N^{\varepsilon 26}$\{2-[2-(2-{2-[2-(2-{(S)-4-Carboxy-4-[10-(4-carboxyphenoxy)decanoylamino]butyrylamino}-ethoxy)ethoxy]acetylamino}ethoxy)ethoxy]acetyl\}, $N^{\varepsilon 37}$-\{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl\}-[Aib$^8$, Arg$^{34}$,Lys$^{37}$]GLP-1(7-37)-OH.
30. A GLP-1 peptide according to any one of the preceding embodiments, wherein said peptide is administered in a composition further comprising one or more pharmaceutically acceptable excipients.
31. A GLP-1 peptide according to embodiment 22, wherein said composition is in the form of a solid dosage form, such as a tablet or a capsule.
32. A GLP-1 peptide according to any one of the preceding embodiments, wherein said peptide is administered in a dosage which provides a steady state average plasma concentration of said peptide of 1-1000 nM.
33. A GLP-1 according to any one of the preceding embodiments, wherein said peptide is administered in a dosage which provides a steady state average plasma concentration of said peptide of 1-300 nM.
34. A GLP-1 according to any one of the preceding embodiments, wherein said peptide is administered in a dosage which provides a steady state average plasma concentration of said peptide of 10-100 nM.
35. A GLP-1 peptide according to any one of the preceding embodiments, wherein said treatment comprises prevention and/or treatment of type 2 diabetes or obesity.
36. A method of oral administration of a pharmaceutically active GLP-1 peptide to a subject, wherein said peptide has plasma half-life in humans of at least 60 hours, and wherein said method comprises the step of administering said peptide every second day or more often in a therapeutically effective amount.
37. A method of oral administration of a low clearance GLP-1 peptide in a therapeutically effective dosage to a subject, wherein the ratio between the plasma half-life in days in humans of said peptide and the dosing interval in days of said peptide is more than 2:1.
38. A method according to any one of the preceding embodiments, wherein the ratio between the plasma half-life in days in humans of said peptide and the dosing interval in days of said peptide is more than 3:1.
39. A method according to any one of the preceding embodiments, wherein the ratio between the plasma half-life in days in humans of said peptide and the dosing interval in days of said peptide is more than 4:1.
40. A method according to any one of the preceding embodiments, wherein the ratio between the plasma half-life in days in humans of said peptide and the dosing interval in days of said peptide is more than 5:1.
41. A method according to any one of the preceding embodiments, wherein the ratio between the plasma half-life in days in humans of said peptide and the dosing interval in days of said peptide is more than 6:1.
42. A method according to any one of the preceding embodiments, wherein the ratio between the plasma half-life in days in humans of said peptide and the dosing interval in days of said peptide is more than 7:1.
43. A method according to any one of the preceding embodiments, wherein the ratio between the plasma half-life in days in humans of said peptide and the dosing interval in days of said peptide is more than 14:1.
44. A method according to any one of the preceding embodiments, wherein plasma half-life is measured after i.v. administration.
45. A method according to any one of the preceding embodiments, wherein plasma half-life is measured after p.o. administration.
46. A method according to any one of the preceding embodiments, wherein said peptide has plasma half-life in humans of at least 1 day.
47. A method according to any one of the preceding embodiments, wherein said peptide has plasma half-life in humans of at least 36 hours.
48. A method according to any one of the preceding embodiments, wherein said peptide has plasma half-life in humans of at least 2 days.
49. A method according to any one of the preceding embodiments, wherein said peptide has plasma half-life in humans of at least 60 hours.
50. A method according to any one of the preceding embodiments, wherein said peptide is administered at least every second day.
51. A method according to any one of the preceding embodiments, wherein said peptide is administered at least once daily.
52. A method according to any one of the preceding embodiments, wherein said peptide is administered at least twice daily.
53. A method according to any one of the preceding embodiments, wherein said peptide is administered in an amount in the range of 0.5-100 mg.
54. A method according to any one of the preceding embodiments, wherein said peptide is administered in an amount in the range of 0.5-50 mg.
55. A method according to any one of the preceding embodiments, wherein said peptide is administered in an amount in the range of 0.5-25 mg.
56. A method according to any one of the preceding embodiments, wherein said peptide is administered in an amount in the range of 1-25 mg.
57 A method according to any one of the preceding embodiments, wherein said peptide is administered in an amount in the range of 5-50 mg.
58. A method according to any one of the preceding embodiments, wherein said peptide is administered in an amount in the range of 0.5-10 mg.
59. A method according to any one of the preceding embodiments, wherein said peptide is administered in an amount in the range of 0.5-5 mg.
60. A method according to any one of the preceding embodiments, wherein said peptide is a GLP-1 peptide.
61 A method according to any one of the preceding embodiments, wherein said peptide is an acylated GLP-1 peptide.
62. A method according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37) or $N^{\epsilon 26}$\{2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl\}, $N^{\epsilon 37}$-\{2-[2-(2-{2-[2-(2-{(S)-4-carboxy-4-[10-(4-carboxy-phenoxy)decanoylamino]butyrylamino}ethoxy)ethoxy]acetylamino}ethoxy)ethoxy]acetyl\}-[$Aib^8$, $Arg^{34}$,$Lys^{37}$]GLP-1(7-37)-OH.
63. A method according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37).
64. A method according to any one of the preceding embodiments, wherein said peptide is $N^{\epsilon 26}$\{2-[2-(2-{2-[2-(2-{(S)-4-Carboxy-4-[10-(4-carboxyphenoxy)decanoylamino]butyrylamino}-ethoxy)ethoxy]acetylamino}ethoxy)ethoxy]acetyl\}, $N^{\epsilon 37}$-\{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl\}-[$Aib^8$, $Arg^{34}$,$Lys^{37}$]GLP-1(7-37)-OH.
65. A method according to any one of the preceding embodiments, wherein said peptide is administered in a composition further comprising one or more pharmaceutically acceptable excipients.
66. A method according to embodiment 22, wherein said composition is in the form of a solid dosage form, such as a tablet or a capsule.
67. A method according to any one of the preceding embodiments, wherein said peptide is administered in a dosage which provides a steady state average plasma concentration of said peptide of 1-1000 nM.
68. A method according to any one of the preceding embodiments, wherein said peptide is administered in a dosage which provides a steady state average plasma concentration of said peptide of 1-300 nM.

69. A method according to any one of the preceding embodiments, wherein said peptide is administered in a dosage which provides a steady state average plasma concentration of said peptide of 10-100 nM
70. A method according to any one of the preceding embodiments, wherein said method comprises prevention and/or treatment of type 2 diabetes or obesity.
71. Use of a GLP-1 peptide in the manufacture of a medicament for oral administration in the treatment of diabetes, wherein said peptide has plasma half-life in humans of at least 60 hours, and wherein said method comprises the step of administering said peptide every second day or more often in a therapeutically effective amount.
72. Use of a low clearance GLP-1 peptide in the manufacture of a medicament for oral administration in the treatment of diabetes, wherein the ratio between the plasma half-life in days in humans of said peptide and the dosing interval in days of said peptide is more than 2:1.
73. Use according to any one of the preceding embodiments, wherein the ratio between the plasma half-life in days in humans of said peptide and the dosing interval in days of said peptide is more than 3:1.
74. Use according to any one of the preceding embodiments, wherein the ratio between the plasma half-life in days in humans of said peptide and the dosing interval in days of said peptide is more than 4:1.
75. Use according to any one of the preceding embodiments, wherein the ratio between the plasma half-life in days in humans of said peptide and the dosing interval in days of said peptide is more than 5:1.
76. Use according to any one of the preceding embodiments, wherein the ratio between the plasma half-life in days in humans of said peptide and the dosing interval in days of said peptide is more than 6:1.
77. Use according to any one of the preceding embodiments, wherein the ratio between the plasma half-life in days in humans of said peptide and the dosing interval in days of said peptide is more than 7:1.
78. Use according to any one of the preceding embodiments, wherein the ratio between the plasma half-life in days in humans of said peptide and the dosing interval in days of said peptide is more than 14:1.
79. Use according to any one of the preceding embodiments, wherein plasma half-life is measured after i.v. administration.
80. Use according to any one of the preceding embodiments, wherein plasma half-life is measured after p.o. administration.
81. Use according to any one of the preceding embodiments, wherein said peptide has plasma half-life in humans of at least 1 day.
82. Use according to any one of the preceding embodiments, wherein said peptide has plasma half-life in humans of at least 36 hours.
83. Use according to any one of the preceding embodiments, wherein said peptide has plasma half-life in humans of at least 2 days.
84. Use according to any one of the preceding embodiments, wherein said peptide has plasma half-life in humans of at least 60 hours.
85. Use according to any one of the preceding embodiments, wherein said peptide is administered at least every second day.
86. Use according to any one of the preceding embodiments, wherein said peptide is administered at least once daily.
87. Use according to any one of the preceding embodiments, wherein said peptide is administered at least twice daily.
88. Use according to any one of the preceding embodiments, wherein said peptide is administered in an amount in the range of 0.5-100 mg.
89. Use according to any one of the preceding embodiments, wherein said peptide is administered in an amount in the range of 0.5-50 mg.
90. Use according to any one of the preceding embodiments, wherein said peptide is administered in an amount in the range of 0.5-25 mg.
91. Use according to any one of the preceding embodiments, wherein said peptide is administered in an amount in the range of 1-25 mg.
92. Use according to any one of the preceding embodiments, wherein said peptide is administered in an amount in the range of 5-50 mg.
93. Use according to any one of the preceding embodiments, wherein said peptide is administered in an amount in the range of 0.5-10 mg.
94. Use according to any one of the preceding embodiments, wherein said peptide is administered in an amount in the range of 0.5-5 mg.
95. Use according to any one of the preceding embodiments, wherein said peptide is a GLP-1 peptide.
96. Use according to any one of the preceding embodiments, wherein said peptide is an acylated GLP-1 peptide.
97. Use according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37) or $N^{\varepsilon 26}${2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl}, $N^{\varepsilon 37}$-{2-[2-(2-{2-[2-(2-{(S)-4-carboxy-4-[10-(4-carboxy-phenoxy)decanoylamino]butyrylamino}ethoxy)ethoxy]acetylamino}ethoxy)ethoxy]acetyl}-[$Aib^8$, $Arg^{34}$,$Lys^{37}$] GLP-1(7-37)-OH.
98. Use according to any one of the preceding embodiments, wherein said peptide is N-epsilon26-[2-(2-{2-[2-(2-{2-[(S)-4-Carboxy-4-(17-carboxyheptadecanoylamino)butyryl-amino]ethoxy}ethoxy)acetylamino]ethoxy}ethoxy)acetyl][Aib8,Arg34]GLP-1-(7-37).
99. A method according to any one of the preceding embodiments, wherein said peptide is $N^{\varepsilon 26}${2-[2-(2-{2-[2-(2-{(S)-4-Carboxy-4-[10-(4-carboxyphenoxy)decanoylamino]butyrylamino}-ethoxy)ethoxy]acetylamino}ethoxy)ethoxy]acetyl}, $N^{\varepsilon 37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[$Aib^8$, $Arg^{34}$,$Lys^{37}$] GLP-1(7-37)-OH.
100. Use according to any one of the preceding embodiments, wherein said peptide is administered in a composition further comprising one or more pharmaceutically acceptable excipients.
101. Use according to embodiment 22, wherein said composition is in the form of a solid dosage form, such as a tablet or a capsule.
102. Use according to any one of the preceding embodiments, wherein said peptide is administered in a dosage which provides a steady state average plasma concentration of said peptide of 1-1000 nM.
103. Use according to any one of the preceding embodiments, wherein said peptide is administered in a dosage which provides a steady state average plasma concentration of said peptide of 1-300 nM.
104. Use according to any one of the preceding embodiments, wherein said peptide is administered in a dosage which provides a steady state average plasma concentration of said peptide of 10-100 nM.
105. Use according to any one of the preceding embodiments, wherein said method comprises prevention and/or treatment of type 2 diabetes or obesity.

EXAMPLES

Preparation of GLP-1 Peptides:
GLP-1 peptides were prepared according to methods known to the person skilled in the art, e.g. as described in example 4 of WO 2006/097537 and in example 2 of WO 2011/080103.
In general, GLP-1 peptides may be prepared by recombinant expression, for example in *E. coli* or *S. cerevisae* (see e.g. WO 2008/034881). Alternatively GLP-1 peptides may be prepared by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999 or liquid phase synthesis. Yet alternatively, a combination of recombinant expression and chemical synthesis may be used for the production of GLP-1 peptides (as e.g. described in WO 2009/083549). Chemical modification by GLP-1 peptides may be performed by standard acylation technology as e.g. described in WO 2010/029159.
Preparation of Tablet Compositions Comprising GLP-1 and SNAC:
Tablet compositions comprising GLP-1 peptide and SNAC (sodium N-(8-(2-hydroxybenzoyl)amino)caprylate) were prepared according to methods known to the person skilled in the art by mixing GLP-1 peptide, SNAC, Microcrystalline cellulose (Avicel PH 101), Povidone K 90 (Kollidon 90F), and Magnesium stearate and roller compacting as e.g. described in WO 2008/028859 (preparation of SNAC) and WO 2003/72195, PCT application PCT/EP2013/055362 and PCT application PCT/EP2013/055363 (methods for preparation of GLP-1 peptide/SNAC compositions).
Analysis of Plasma Samples Using LOCI:
The plasma was analysed for active peptide ingredient using a Luminescence Oxygen Channeling Immunoassay (LOCI). The LOCI assay employs donor beads coated with streptavidin and acceptor beads conjugated with a monoclonal antibody binding to a mid-molecular region of active peptide ingredient. The other monoclonal antibody, specific for an N-terminal epitope, was biotinylated. In the assay the three reactants were combined with the active peptide ingredient which form a two-sited immuno-complex. Illumination of the complex releases singlet oxygen atoms from the donor beads which channels into the acceptor beads and trigger chemiluminescence which was measured in the EnVision plate reader. The amount of light was proportional to the concentration of active peptide ingredient and the lower limit of quantification (LLOQ) in plasma was 100 pM.
Alternative Analysis of Plasma Samples Using LC-MS:
The plasma was analysed for active peptide ingredient using LC-MS (Liquid Chromatography-Mass Spectrometry) as known to the person skilled in the art. The LC-MS system consisted of Waters Acquity UPLC system (Waters) consisting of an autosampler (Model Acq-SM), pump (Model Acq-BSM), column oven (Model Acq-SM), detector (Model Acq-TUV) and LTQ Orbitrap XL (Thermo Fisher). RP-HPLC separation was achieved using a linear gradient of acetonitrile in 0.1% formic acid using CSH C18 column (Waters, 1×150 mm) with a flow rate of 0.1 ml/min at 45° C.

Example 1: N-epsilon26-[2-(2-{2-[2-(2-{2-[(S)-4-Carboxy-4-(17-carboxyheptadecanoyl-amino)butyrylamino]ethoxy}ethoxy)acetylamino]ethoxy}ethoxy)acetyl][Aib8,Arg34]GLP-1-(7-37) (GLP-1 peptide 1) in a SNAC Formulation A pharmacokinetic study was carried out to determine plasma half-life of the GLP-1 peptides after p.o. administration to humans.
Subjects were administered p.o. GLP-1 peptide 1 in a SNAC formulation. Blood samples were drawn at predefined time points after dosing, and samples were analysed for concentration of the GLP-1 peptide. Based on these measurements plasma concentration versus time profile were plotted and a non-compartmental pharmacokinetic analysis of the data was performed. The variability in plasma concentration was determined as % CV for both $C_{max}$ and AUC. The amount of SNAC in the tablet composition was 300 mg. The results are presented in Table 1.

TABLE 1

| | % CV | |
| --- | --- | --- |
| Dosing regimen of GLP-1 peptide 1 | AUC | Cmax |
| 10 mg/day for 70 days* | 73% (Day 70) | 74% (Day 70) |
| 20 mg/day for 70 days* | 67% (Day 69) | 62% (Day 69) |
| 40 mg/day for 70 days* | 78% (Day 69) | 80% (Day 69) |
| 40 mg/day for 70 days** | 55% (Day 69) | 54% (Day 69) |
| 10 mg, single dose* | 105% | 113% |

*Subjects were healthy.
**Subjects had type 2 diabetes.

These results show that variability in plasma exposure of the GLP-1 peptide was significantly reduced when administering 10, 20 or 40 mg GLP-1 peptide 1 daily for 70 days compared to a single dose of 10 mg GLP-1 peptide 1 to humans.

Example 2: N-epsilon26-[2-(2-{2-[2-(2-{2-[(S)-4-Carboxy-4-(17-carboxyheptadecanoyl-amino)butyrylamino]ethoxy}ethoxy)acetylamino]ethoxy}ethoxy)acetyl][Aib8,Arg34]GLP-1-(7-37) (GLP-1 peptide 1) in SNAC Formulation A pharmacokinetic study was carried out to determine plasma half-life of the GLP-1 peptides after p.o. administration to Beagle dogs.
Dogs were administered p.o. GLP-1 peptide 1 in a SNAC formulation. Blood samples were drawn at predefined time points after dosing, and samples were analysed for concentration of the GLP-1 peptide. Based on these measurements plasma concentration versus time profile were plotted and a non-compartmental pharmacokinetic analysis of the data was performed. The variability in plasma concentration of the GLP-1 peptide was determined as % CV for AUC. The amount of SNAC in the tablet composition was 300 mg. The results are presented in Table 2.

TABLE 2

| Dosing regimen of GLP-1 peptide 1 | % CV AUC |
|---|---|
| 5 mg/day for 7 days | 67% |
| 15 mg, single dose | 131-167% |

These results show that variability in plasma exposure of the GLP-1 peptide was significantly reduced when administering 5 mg GLP-1 peptide 1 daily for 7 days compared to a single dose of 15 mg GLP-1 peptide 1.

Example 3: $N^{\varepsilon 26}$\{2-[2-(2-\{2-[2-(2-\{(S)-4Carboxy-4-[10-(4-carboxyphenoxy)decanoylamino]-butyrylamino\}ethoxy)ethoxy]acetylamino\}ethoxy)ethoxy]acetyl\}, $N^{\varepsilon 37}$-\{2-[2-(2-\{2-[2-(2-\{(S)-4-carboxy-4-[10-(4-carboxyphenoxy)decanoylamino]butyrylamino\}ethoxy)ethoxy]acetyl-amino\}ethoxy)ethoxy]acetyl\}-[Aib$^8$,Arg$^{34}$,Lys$^{37}$]GLP-1(7-37)-OH (GLP-1 peptide 2) in SNAC Formulation A pharmacokinetic study was carried out to determine plasma half-life of the GLP-1 peptides after p.o. administration to Beagle dogs.

Dogs were administered p.o. GLP-1 peptide 2 in a SNAC formulation. Blood samples were drawn at predefined time points after dosing, and samples were analysed for concentration of the GLP-1 peptide. Based on these measurements plasma concentration versus time profile were plotted and a non-compartmental pharmacokinetic analysis of the data was performed. The variability in plasma concentration of the GLP-1 peptide was determined as % CV for AUC. The amount of SNAC in the tablet composition was 300 mg. The results are presented in Table 3.

TABLE 3

| Dosing regimen of GLP-1 peptide 2 | % CV AUC |
|---|---|
| 10 mg/day for 7 days | 33% |
| 10 mg, single dose | 67% |

These results show that variability in plasma exposure of the GLP-1 peptide was significantly reduced when administering 10 mg GLP-1 peptide 2 daily for 7 days compared to a single dose of 10 mg GLP-1 peptide 2.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for treating diabetes and/or obesity in a subject in need of such treatment, said method comprising:
    orally administering to said subject a therapeutically effective amount of a solid oral dosage form composition comprising a glucagon-like peptide-1 (GLP-1) peptide and an enhancer,
    wherein:
        (a) the GLP-1 peptide is an acylated GLP-1 analogue having 3 amino acid substitutions or less relative to native GLP-1 (7-37) peptide, and has a plasma half-life in humans of at least 60 hours;
        (b) the enhancer is a salt of N-(8-(2-hydroxybenzoyl)amino)caprylic acid; and
        (c) said composition is administered such that the ratio between the plasma half-life in days in humans of said peptide and the dosing interval in days of said composition is more than 2:1.

2. The method of claim 1, wherein said GLP-1 peptide is selected from the group consisting of N-epsilon26-[2-(2-\{2-[2-(2-\{2-[(S)-4-Carboxy-4-(17-carboxyheptadecanoylamino)butyryl-amino]ethoxy\}ethoxy)acetylamino]ethoxy\}ethoxy)acetyl][Aib8,Arg34]GLP-1-(7-37) (semaglutide), and
$N^{\varepsilon 37}$\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$_8$,Arg$_{34}$,Lys$_{37}$]GLP-1(7-37)-OH.

3. The method of claim 2, wherein said composition is administered every second day or more frequently.

4. The method of claim 3, wherein said composition is administered once daily.

5. The method of claim 3, wherein said composition is in the form of a tablet, capsule, sachet, or granules.

6. The method of claim 5, wherein said composition is in the form of a tablet.

7. The method of claim 3, wherein said GLP-1 peptide is semaglutide.

8. The method of claim 6, wherein the enhancer is sodium N-(8-(2-hydroxybenzoyl)amino)caprylate (SNAC).

9. The method of claim 8, wherein said composition comprises 2-40 mg semaglutide and 200-400 mg SNAC.

10. The method of claim 9, wherein said composition is administered every second day or more frequently.

11. The method of claim 10, wherein said composition is administered once daily.

12. The method of claim 9, wherein said composition is in the form of a tablet, capsule, sachet, or granules.

13. The method of claim 12, wherein said composition is in the form of a tablet.

14. A method for treating diabetes and/or obesity in a subject in need of such treatment, said method comprising:
    orally administering to said subject a therapeutically effective amount of a solid oral dosage form composition comprising a glucagon-like peptide-1 (GLP-1) peptide and an enhancer,
    wherein the GLP-1 peptide is:
        (a) selected from the group consisting of N-epsilon26-[2-(2-\{2-[2-(2-\{2-[(S)-4-Carboxy-4-(17-carboxyheptadecanoylamino)butyryl-amino]ethoxy\}ethoxy)acetylamino]ethoxy\}ethoxy)acetyl][Aib8,Arg34]GLP-1-(7-37) (semaglutide) and $N^{\varepsilon 37}$ \{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$_8$,Arg$_{34}$,Lys$_{37}$]GLP-1(7-37)-OH; and
        (b) has a plasma half-life in humans of at least 60 hours;
    wherein the enhancer is sodium N-(8-(2-hydroxybenzoyl)amino)caprylate (SNAC); and
    wherein said composition is administered every second day or more frequently.

15. The method of claim 14, wherein said composition comprises 2-40 mg semaglutide and 200-400 mg SNAC.

16. The method of claim 15, wherein said composition is administered once daily.

17. The method of claim 15, wherein said composition is in the form of a tablet, capsule, sachet, or granules.

18. The method of claim 17, wherein said composition is in the form of a tablet.

19. The method of claim 8, wherein said composition comprises 300 mg of SNAC.

20. The method of claim 15, wherein said composition comprises 300 mg of SNAC.

21. A method for treating diabetes and/or obesity in a subject in need of such treatment, said method comprising:

orally administering to said subject a therapeutically effective amount of a solid oral dosage form composition comprising a glucagon-like peptide-1 (GLP-1) peptide and an enhancer, wherein:

(a) the GLP-1 peptide is N-epsilon26-[2-(2-{2-[2-(2-{2-[(S)-4-Carboxy-4-(17-carboxyheptadecanoylamino) butyryl-amino]ethoxy}ethoxy)acetylamino] ethoxy}ethoxy)acetyl][Aib8,Arg34]GLP-1-(7-37) (semaglutide) and has a plasma half-life in humans of at least 60 hours;

(b) the enhancer is sodium N-(8-(2-hydroxybenzoyl) amino)caprylate (SNAC); and (c) the composition is administered once daily.

22. The method of claim 21, wherein said composition comprises 2-40 mg semaglutide and 200-400 mg SNAC.

23. The method of claim 22, wherein said composition comprises 300 mg of SNAC.

\* \* \* \* \*